United States Patent [19]

Schulteis

[11] 4,439,224

[45] Mar. 27, 1984

[54] PLANT GROWTH REGULATOR AND METHOD FOR THE USE THEREOF

[75] Inventor: David T. Schulteis, Fresno, Calif.

[73] Assignee: Wilbur-Ellis Company, Fresno, Calif.

[21] Appl. No.: 305,496

[22] Filed: Sep. 25, 1981

Related U.S. Application Data

[63] Continuation of Ser. No. 173,112, Jul. 28, 1980, abandoned.

[51] Int. Cl.³ .............................................. A01N 43/40
[52] U.S. Cl. ............................................ 71/76; 71/94; 71/121
[58] Field of Search ............................. 71/121, 94, 76

[56] References Cited

U.S. PATENT DOCUMENTS 3,854,928 12/1974 Buckman et al. ...................... 71/121
3,905,798 9/1975 Zeeh et al. .............................. 71/94
4,153,445 5/1979 Kappel .................................... 71/94
4,265,656 5/1981 Lürssen ................................... 71/94

FOREIGN PATENT DOCUMENTS 2815443 10/1979 Fed. Rep. of Germany ......... 71/76
2815345 10/1979 Fed. Rep. of Germany ......... 71/76

OTHER PUBLICATIONS

Towne et al., "Interaction of Surfactant, etc.," (1978), Weed Sci. 26, pp. 182–188, (1978).

Primary Examiner—Glennon H. Hollrah
Attorney, Agent, or Firm—Huebner & Worrel

[57] ABSTRACT

A plant growth regulator having a composition including poly[oxyethylene(dimethyliminio)ethylene(dimethyliminio) ethylene dichloride]N,N-dimethylpiperidinium chloride and method for the application thereof.

4 Claims, 1 Drawing Figure

PLANT GROWTH REGULATOR AND METHOD FOR THE USE THEREOF

CROSS-REFERENCE TO A RELATED APPLICATION

This is a continuation application of United States patent application Ser. No. 173,112 filed July 28, 1980, now abandoned.

BACKGROUND OF THE INVENTION

1. Field of the Invention

The present invention relates to novel compositions and the use thereof in regulating the growth of plants and more particularly to such compositions which operate to increase the crop yield of plants to which they are applied and to inhibit undesirable rank growth.

2. Description of the Prior Art

In recent years agricultural methods have undergone revolutionary changes which include reduction of tillage and cultivation, crowded planting of new and old varieties of crop plants, and increased use of fertilizers with the ultimate goal of increased yields of crop plants per acre together with an overall reduction in labor requirements through an increased use of mechanical equipment. Although such new agricultural methods constitute advances in the art, the results have not been entirely satisfactory.

For example, while the mechanical harvesting of such crops as cotton, tomatoes and beans has lowered production costs, it has also created new problems. In the case of cotton, mechanical harvesting has created perplexing problems at gins and textile mills. Such mechanically harvested cotton absorbs moisture from the spindles of the harvester and contains considerably more than the normal 5 to 15 percent of trash present in hand-picked cotton. Particularly bothersome is leaf material which is one of the most difficult types of trash to remove. This additional moisture and trash in mechanically harvested cotton frequently complicates ginning operations and raises the costs of textile manufacturing by requiring additional steps in cleaning the cotton at the mill.

Recent efforts have been directed toward the development of various chemical treatments for the crop plant in an effort to overcome the objectionable attributes of mechanically harvested cotton. For example, processes have been suggested in recent years which have as their objective to provide increased yields of the desired crop and/or to inhibit rank growth. Such processes have been effective in some respects. However, some of the prior art methods require the use of expensive surfactants in order to obtain satisfactory application of the chemical product to the plant. Other prior art methods produce an insufficient increase in the crop yield and/or decreases in rank growth for economic utilization.

Therefore, it has been recognized that there is a need in agriculture for the development of a plant growth regulator and method for the use thereof which is capable of substantially increasing the yield of such crops as cotton, while substantially decreasing rank growth and which can be employed dependably and economically in a manner fully compatible with other agricultural and manufacturing processes.

SUMMARY OF THE INVENTION

Therefore, it is an object of the present invention to provide an improved plant growth regulator and method for the use thereof.

Another object is to provide such a plant growth regulator and method which are capable of substantially increasing crop yield while inhibiting rank growth to a degree not heretofore achieved.

Another object is to provide such a plant growth regulator and method which are particularly well suited to use on cotton plants.

Another object is to provide such a plant growth regulator and method whih can be employed dependably and in a manner fully compatible with other agricultural and manufacturing practices.

Another object is to provide such a plant growth regulator and method which are substantially less expensive than prior art plant growth regulators and methods.

These and other objects and advantages will become apparent upon reference to the accompanying drawing and description.

DESCRIPTION OF THE PREFERRED EMBODIMENT

Figure 1:
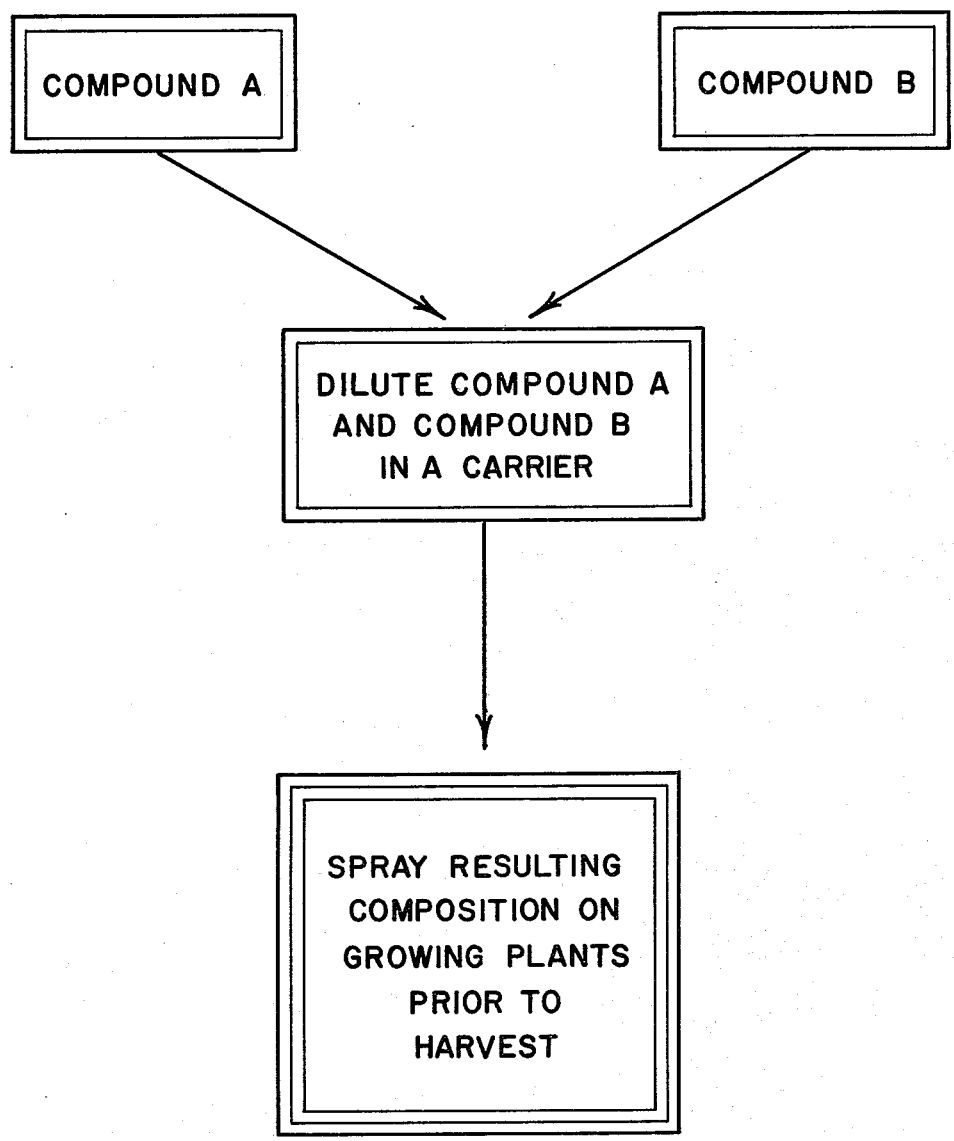
FIG. 1 is a diagrammatic view depicting the steps in the formulation of the plant growth regulator and method for the use thereof of the present invention.

Referring more particularly to the drawing, the plant growth regulator of the present invention is a composition having as active components poly[oxyethylene(-dimethyliminio)ethylene(dimethyliminio)ethylene dichloride], designated in the drawing and hereinafter as "Compound A", and N,N-dimethyl piperidinium chloride, designated in the drawing and hereinafter as "Compound B". Compound A can be prepared following the method described in Example 1 of U.S. Pat. No. 3,771,989, which disclosure is hereby incorporated by reference and made a part of this application. Compound A is also available commercially as a water-soluble composition under the trademark "WSCP" containing on a weight basis 60% Compound A and 40% inert ingredients. Compound B is available commercially as a water-soluble composition under the trademark "PIX" containing on a weight basis 4.2% Compound B and 95.8% inert ingredients. For purposes of illustrative convenience, these water soluble commercially available compositions will hereinafter be referred to by their respective trademarks "WSCP" and "PIX". However, it will be understood that as used herein and in the Examples to follow, "active components" refers to Compound A and Compound B and not the commercially available compositions "WSCP" and "PIX".

The plant growth regulator of the present invention is conveniently applied by forming an aqueous solution thereof and spraying the aqueous solution onto the foliage of the plant using conventional spraying equipment. Compound A and Compound B are water-soluble and thus an aqueous solution containing Compound A and Compound B is readily prepared and there are no unusual mixing or handling problems associated with its formation or application using conventional spraying equipment. Usually about 0.5 to 95 percent by weight of the active components will be included in such an aqueous solution.

Water is preferred as the carrier or diluent because it is readily available, is economical, and its use avoids the need for the use of any other solvent, carrier, or surfactant. However, the subject invention is not limited to water as the carrier since other inert carriers can also be used. Liquid compositions including the active components described above can be prepared by admixing the active components with suitable solvents, together with a suitable surface active agent. Typical of the liquid media other than water which can be employed as carriers are aliphatic alcohols, ketones, benzene, toluene, and the like. The active components usually make up from about 0.5 to about 95 percent of these liquid compositions, which can be subsequently diluted, as with water, to the desired concentration for application to plants and soil. Such concentrates as prepared by the manufacturer have the advantage that the user need only mix them with a locally available carrier, preferably water, thereby reducing shipping costs and providing a product which can be used with a minimum of equipment and effort.

Compositions in the form of wettable powders can include one or more surface active agents, such as wetting or dispersing agents. The surface active agents cause the compositions of wettable powders to disperse easily in water.

Suitable surface active agents which may be used include anionic, cationic, or nonionic types such as disclosed by A. M. Schwartz, J. W. Perry, and J. Berch in "Surface Active Agents and Detergents", vol. II, Interscience Publishers, Inc., New York, New York (1958).

In accordance with the subject invention, the plants are treated with the plant growth regulator hereof from about two to twelve weeks prior to harvest, with the preferred time for treatment of cotton plants being from five to eight weeks prior to harvest. Best results are obtained when about 2.0 to about 5.0 pounds, and occasionally up to 10 pounds, of the active components are applied per acre of the plant crop, although as little as 1 pound, and sometimes even less, per acre can provide a beneficial effect. More than 10 pounds per acre is normally not preferred because of diminished improvement and increased costs, although it will be appreciated that the optimum amount depends on many factors such as density of the plants, type and/or variety of the plants, efficiency of the application and the like. In this regard, rainfall within a few hours of the application is deleterious, and to the extent possible, treatment should take place when rainfall is not imminent. Where Compound A is used in the form of the commercially available product WSCP, it has been found preferable to dilute WSCP with water at the ratio of 3 pints WSCP per 100 gallons water plus the preferred amount of the product containing Compound B sold under the trademark PIX. For purposes of clarity and as a basis for considering the examples hereinafter set forth, it will be recalled that the product sold under the trademark WSCP contains on a weight basis 60% Compound A and 40% inert ingredients. The product sold under the trademark PIX contains by weight 4.2% Compound B and 95.8% inert ingredients. In all of the examples and tables to follow it will be understood that, except as otherwise indicated using the trademarks WSCP or PIX, the proportional mixture ratios and rates of application are of Compound A and Compound B. This is true even though these compounds were applied in the form of WSCP and PIX respectively.

In order to disclose the subject invention still more clearly, attention is invited to the following illustrative examples. It is understood, however, that these examples are merely illustrative and that the subject invention is not to be limited to the specific conditions or details set forth. In the following examples, all parts are by weight unless otherwise indicated.

EXAMPLE I

In order to determine the preferred ratio of PIX to WSCP in the plant growth regulator of the subject invention, PIX was diluted with varying amounts of water (1 pint of PIX per 10 to 60 gallons of water in increments of 10 gallons). Two cotton fields, one located in Arizona and the other in California were each divided into several acre plots and then the individual plots were each treated by spraying with a mixture of the two active components as summarized in Table 1.

TABLE 1

| Gallons/Acre Applied | PPM Compound A In Solution | PPM Compound B In Solution | Ratio Compound A to Compound B |
| --- | --- | --- | --- |
| 10 | 2600 | 528 | 5:1 |
| 20 | 2600 | 264 | 9:1 |
| 30 | 2600 | 176 | 14:1 |
| 40 | 2600 | 132 | 19:1 |
| 50 | 2600 | 105 | 24:1 |
| 60 | 2600 | 88 | 29:1 |

In the foregoing test, "ppm" represents parts of the active Compound A or Compound B as specified per million parts of water. The application rate for WSCP was three pints per one hundred gallons of water. The application rate for PIX was one pint per acre. Therefore, as the total gallons of plant regulator applied per acre increased, the concentration of PIX in the plant regulator applied decreased.

These tests after the several plots were harvested indicated that improved results were obtained by the use of the plant growth regulator of the subject invention as compared to the control in that both yield and the quality of the cotton were improved as compared to the control plot where PIX was employed by itself. As to the preferred ratio of the two compounds, these tests indicated that the amount of Compound A should preferably be in the range of from about 2.5 to about 19 parts per part of Compound B.

In Examples II and III hereinafter set forth, where PIX was used alone or with the product sold under the trademark "Agradex" or with the product sold under the trademark "X-77", the amount of PIX used was equal to 1.0 pint per acre. When PIX was used with WSCP, one pint of a solution comprising 19 parts of WSCP per part of PIX was employed as a spray per acre. As in Example I, WSCP was used in Examples II and III at the rate of 3 pints per 100 gallons of water.

EXAMPLE II

A uniform field of Pima cotton was selected in the Tempe, Ariz. area for experimental trials using PIX in combination with several spray adjuvants. Previous field tests with PIX have demonstrated increased yields and height reduction of Pima cotton only if a high rate is used (1½–2 pints per acre) or an application of 1 per acre followed 7–10 days later with another application at 1 pint per acre. Several spray additives were tested with PIX to investigate a possible increase in activity by incorporating them into the spray solutions. In addition to WSCP, PIX was tested without WSCP, but with a nonionic mixture of 90 percent active alkyl aryl polyoxyetheylene glycols widely used commercially as an agricultural spreader-wetting agent and sold under the trademark "X-77" and with a combination of 98 percent active nonionic surfactants with a phytobland oil widely used agriculturally as an activator-penetrator type spray adjuvant and sold under the trademark "Agradex".

The rates of application for the various products and combination of products as well as the height measurements and yield results are presented in the following table. Each treatment was replicated four times.

TABLE 2

| Treatment | Rate Pints/ Acre | PPM Active Composition In Solution | Boll Clustering | Height of Plants Inches | Yield |
|---|---|---|---|---|---|
| Control | — | — | No | 52–54 | 4015 |
| PIX | 1.0 | 132 | No | 48 | 3905 |
| PIX | 1.5 | 198 | No | 44 | 4318 |
| PIX | 2.0* | 264 | Yes | 40 | 3878 |
| PIX + Agradex | 1.0 | 132 + 2828 | No | 48 | 4345 |
| PIX + X-77 | 1.0 | 132 + 1155 | No | 48 | 4015 |
| PIX + WSCP | 1.0* | 132 + 2600 | Yes | 40–42 | 4483 |

"Boll Clustering", as it appears in Table 2, describes a plant which has an unusual number of bolls clustered near the top of the cotton plant. "Yield" in Table 2 represents the pounds of seed cotton/acre. The middle two rows of each treatment were harvested. The treatments marked with asterisks in Table 2 were on more mature plants than any of the other treatments in the Table. They appeared to increase maturity of the cotton plants. In the last three treatments listed in the table, Agradex contained 98% by weight of the active ingredients listed above and Agradex was applied at the rate of 2 pints per 100 gallons of water plus 1 pint PIX as indicated; X-77 contained 80% by weight of the active ingredients listed above and X-77 was applied at the rate of 1 pint per 100 gallons of water plus 1 pint PIX as indicated; and WSCP, as in previous examples, contained 60% by weight Compound A and was applied at the rate of 3 pints per 100 gallons of water plus 1 pint PIX as indicated.

EXAMPLE III

An Acala SJ 2 cotton field located in the San Joaquin Valley of California was selected for treatment because of the field's previous history of growing very rank cotton. Several contiguous, six acre blocks were selected for treatment with PIX. PIX was tested along and in combination with WSCP. The results of this field trial are presented in the following table.

TABLE 3

| Treatment | Rate Pints/ Acre | PPM Active Composition In Solution | Boll Clustering | Height of Plant Inches | Yield Pounds |
|---|---|---|---|---|---|
| Control | — | — | No | 49.96 | 3341 |
| PIX | 1.0 | 132 | No | 40.43 | 2990 |
| PIX + WSCP | 1.0 | 132 + 2600 | Yes | 39.33 | 3480 |

In both of these examples there was an increase in the activity of PIX, both in plant yield increase and height reduction, when WSCP was added to the spray solution. Again, in the last treatment of Table 3, 1 pint of PIX plus 3 pints WSCP per 100 gallons of water were applied per acre.

Although somewhat better results are obtained by following the first spraying application in about 7 to 10 days with a second application, such a procedure is generally not desirable as the resultant improvement is rather limited, and as a consequence, does not justify the additional costs incurred.

EXAMPLE IV

To evaluate the effect of PIX, WSCP, and a preferred mixture of PIX and WSCP, a series of greenhouse tests were carried out in which 20 cotton plants were carefully selected as to equality in size and health and divided into four groups of five plants each and designated Plot Nos. 1, 2, 3, and 4. At the beginning of the tests, each of the plants was sprayed with an amount of water at a rate equivalent to 40 gallons per acre. Plot No. 1 was sprayed with water only, Plot No. 2 with water plus WSCP, Plot No. 3 with water plus PIX, and Plot No. 4 with water plus WSCP and PIX. The amounts of the active ingredients based on 40 gallons of water used as spray is indicated in Table 4 below. At the end of one week, the height of all the plants were measured and the experiments and the results are summarized in Table 4.

TABLE 4

| Plot | Treatment Compound A | Compound B | Plant Height In Centimeters | Plant Height Difference In Centimeters |
|---|---|---|---|---|
| No. 1 | 0.0 | 0.0 | 3.90 | 0.0 |
| No. 2 | 2582.3 | 0.0 | 4.54 | +0.64 |
| No. 3 | 0.0 | 131.8 | 3.34 | −0.56 |
| No. 4 | 2582.3 | 131.8 | 1.16 | −2.74 |

Compund A, as shown in Table 4, was applied in the commercially available form WSCP at a rate equivalent to 3 pints of WSCP per 100 gallons of water. Compound B was applied in the commercially available form PIX at a rate equivalent to 1 pint of PIX per acre in 40 gallons of water per acre.

The foregoing data demonstrates that a mixture comprising Compound A and Compound B was very effective in causing growth reduction, a result that is particularly unexpected in view of the fact that when the plant is treated with Compound A alone such a treatment caused an increase in growth. It has also been noted that when a plant is treated with Compound B alone, the results of such a treatment are generally not apparent until two weeks after the treatment. However, the application of the plant growth regulator of the present invention containing Compound A and Compound B as active ingredients demonstrates a color change within 7 days after the treatment.

EXAMPLE V

In this example, the procedure of Example IV was followed in which four plots of five cotton plants each were sprayed as previously described in that example, but in the present example the effect of the treatment at the 7th node was noted. This procedure was followed because it was noted that there was no significant change in height at the first to the 6th nodes. The experiments and results are summarized in Table 5.

TABLE 5

| Plot | Treatment PPM of Active Composition Solution Per Acre | | Height of 7th Node In Centimeters | Difference In Centimeters |
| --- | --- | --- | --- | --- |
| | Compound A | Compound B | | |
| No. 1 | 0.0 | 0.0 | 3.38 | 0.0 |
| No. 2 | 2582.3 | 0.0 | 3.62 | +0.24 |
| No. 3 | 0.0 | 131.8 | 2.24 | −1.14 |
| No. 4 | 2582.3 | 131.8 | 1.74 | −1.64 |

The form and rates of application were the same as given with respect to Table 4.

These data also show that there is a significant decrease in the height of the 7th node in the cotton plants, especially where Compound A and Compound B are applied together.

The foregoing examples have demonstrated that the plant growth regulator of the present invention and method for the use thereof permit an increase in plant crop yield and a decrease in plant growth to a degree not heretofore achieved in the art. Furthermore, it is apparent that a synergistic effect occurs such that much less of the more expensive Compound B need to be used for the given desired effect thereby substantially reducing the cost involved when compared with the use of Compound B alone as a plant growth regulator.

Therefore, the plant growth regulator and method for use thereof of the present invention operate to increase crop yield and decrease rank growth to an extent not previously possible, at a cost which is fully compatible with economical operation and in a manner not requiring expensive or time consuming procedures.

While the composition and method of the instant invention are described in terms of particular ingredients, and ranges thereof, to be used, it is obvious that modifications and variations in the nature and proportions of the ingredients may be made without departing from the spirit and scope of the invention, which is not to be limited to the illustrative details disclosed.

The invention having thus been described, what is claimed and desired to be secured by Letters Patent is:

1. A method of regulating the growth of cotton plants comprising applying to the foliage of the cotton plants prior to harvest a composition consisting essentially of on a weight basis: a mixture of about 20 parts of poly[oxyethylene(dimethyliminio)ethylene(dimethyliminio)ethylene dichloride] to about 1 part N,N-dimethylpiperidinium chloride diluted in an inert carrier and applied in an amount sufficient to inhibit the growth of the cotton plants and increase the yield thereof.

2. A plant growth regulator composition for cotton plants consisting essentially of an effective amount of a mixture of about 20 parts poly[oxyethylene(dimethyliminio)ethylene(dimethyliminio)ethylene dichloride] per part N,N-dimethylpiperidinium chloride diluted in an inert carrier.

3. A plant growth regulator consisting essentially of a composition of an effective amount of poly[oxyethylene(dimethyliminio)ethylene(dimethyliminio)ethylene dichloride] per part N,N-dimethylpiperidinium chloride in an inert carrier.

4. A method of regulating the growth of plants comprising applying to the foliage of the plants prior to harvest a composition consisting essentially of a mixture of poly[oxyethylene(dimethyliminio)ethylene(dimethyliminio)ethylene dichloride] and N,N-dimethylpiperidinium chloride in a carrier and applied in an amount sufficient to inhibit the growth of the plants and increase the yield thereof.

* * * * *

UNITED STATES PATENT AND TRADEMARK OFFICE
CERTIFICATE OF CORRECTION

PATENT NO. : 4,439,224

DATED : March 27, 1984

INVENTOR(S) : David T. Schulteis

It is certified that error appears in the above-identified patent and that said Letters Patent are hereby corrected as shown below:

Column 2, line 14, delete "whih" and substitute ---which---.

Column 4, line 64, between "1" and "per" insert ---pint---.

Column 5, line 54, delete "along" and substitute ---alone---.

Column 6, line 39, delete "Compund" and substitute ---Compound---.

Signed and Sealed this

Fourth Day of September 1984

[SEAL]

Attest:

GERALD J. MOSSINGHOFF

Attesting Officer     Commissioner of Patents and Trademarks